United States Patent
Kerkis

(10) Patent No.: US 9,498,498 B2
(45) Date of Patent: Nov. 22, 2016

(54) ADIPOSE TISSUE MESENCHYMAL STEM CELLS AND METHODS OF USE TO TREAT OR INHIBIT UTERINE DISORDERS

(71) Applicant: AVITA INTERNATIONAL LTD., Tortola (VG)

(72) Inventor: Irina Kerkis, Sao Paulo (BR)

(73) Assignee: Avita International Ltd., Tortola (VG)

( * ) Notice: Subject to any disclaimer, the term of this patent is extended or adjusted under 35 U.S.C. 154(b) by 32 days.

(21) Appl. No.: 14/211,773

(22) Filed: Mar. 14, 2014

(65) Prior Publication Data

US 2014/0271572 A1    Sep. 18, 2014

Related U.S. Application Data

(60) Provisional application No. 61/794,674, filed on Mar. 15, 2013.

(51) Int. Cl.
*A61K 35/28* (2015.01)
*A61K 9/00* (2006.01)

(52) U.S. Cl.
CPC .............. *A61K 35/28* (2013.01); *A61K 9/0034* (2013.01)

(58) Field of Classification Search
None
See application file for complete search history.

(56) References Cited

U.S. PATENT DOCUMENTS

2013/0209422 A1*  8/2013  Kang et al. .................. 424/93.7

FOREIGN PATENT DOCUMENTS

WO    WO 2012/026712    *  3/2012    ............ A61K 38/03

OTHER PUBLICATIONS

Mambelli et al., "A novel strategy of mesenchymal stem cells delivery in the uterus of mares with endometrosis", Theriogenology, epublished Dec. 25, 2012, vol. 79, pp. 744-750.*
Nagori et al., "Endometrial regeneration using autologous adult stem cells followed by conception by in vitro fertilization in a patient of severe Asherman's syndrome", Journal of Human Reproductive Sciences, 2011, vol. 4, Issue No. 1, pp. 43-48.*
Strioga et al., "Same or Not the Same? Comparison of Adipose Tissue-derived Versus Bone Marrow-Derived Mesenchymal Stem and Stromal cells", Stem Cells, prepublished online Apr. 3, 2012, vol. 21, No. 14, pp. 2724-2752.*

* cited by examiner

*Primary Examiner* — Laura Schuberg
(74) *Attorney, Agent, or Firm* — Rodney J. Fuller; Booth Udall Fuller, PLC

(57) ABSTRACT

There is a high stem cell therapy potential in the field of reproductive disorders. Endometriosis is a common finding in women with infertility. In addition endometriosis is the major problem in the veterinary field. In the disclosed invention we provide a method of application and use of adipose tissue derived stem cell to treat fertility and pregnancy related disorders, especially endometriosis in mammalian objects.

29 Claims, 9 Drawing Sheets
(9 of 9 Drawing Sheet(s) Filed in Color)

ADIPOSE TISSUE MESENCHYMAL STEM CELLS AND METHODS OF USE TO TREAT OR INHIBIT UTERINE DISORDERS

CROSS-REFERENCE TO RELATED APPLICATIONS

This document claims the benefit of the filing date of U.S. Provisional Patent Application 61/794,674, entitled "ADIPOSE TISSUE MESENCHYMAL STEM CELLS AND METHODS OF USE TO TREAT OR INHIBIT UTERINE DISORDER" to Kerkis, which was filed on Mar. 15, 2013, the contents of which are hereby incorporated by reference.

BACKGROUND

1. Field of the Invention

Aspects of the disclosed invention relate to a method of application and use of adipose tissue derived stem cells for the treatment of mammalian uterine disorders including fertility and pregnancy related disorders, particularly endometriosis.

2. Description of the Related Art

Healthy and undamaged uterine cavity and endometrial lining are essential in order to conceive and maintain a full term pregnancy. There are various conditions related to the uterine cavity or the lining that can cause or contribute to reproductive problems such as infertility or recurrent miscarriage. Such conditions include endometriosis, poor endometrium or a thin uterine lining, uterine polyps and fibroids, intrauterine adhesions and uterine cavity scar tissue.

The implantation phase of the mammalian embryo requires a delicate interchange between the embryo and its mother. For this phase to be successful a receptive and healthy endometrium is required (Giudice L C (1999) Potential biochemical markers of uterine receptivity. Hum Reprod 14(Suppl),3-16). Reduced endometrial receptiveness is found in a growing number of unexplained infertilities (Lessey B A, Castelbaum A J, Sawin S W and Sun J (1995) Integrins as markers of uterine receptivity in women with primary unexplained infertility. Fertil Steril 63,535-542). Therefore, an inadequate endometrium can be considered as a main fertility-determining factor.

Although knowledge on molecular mechanisms in the endometrium has increased tremendously, translation of this basic research into daily clinical routine is rather limited. Moreover, endometriosis is an extremely common condition, which affects approximately 15% of women in their reproductive years. It is a condition wherein the endometrium is found in ectopic locations outside the uterus. Such misplaced tissue may implant on the ovaries, uterus, bowel, bladder utero-sacral ligaments, or peritoneum. It is a degenerative disease of uterine glands and surrounding stroma that leads to infertility (Kenney R M. The etiology, diagnosis and classification of chronic degenerative endometritis. Equine Vet J 1992; 25:186, Schoon H A, Schoon D, Klug E. Uterusbiopsien als Hilfsmittel fur Diagnose and Prognose von Fertilitatsstorungen der Stute. Pferdeheilkunde 1992; 8:355-362). Uterine glands secretions are considered essential to embryo implantation, fetal development and survival. Presently, endometrosis is defined as an active or inactive periglandular and/or stromal endometrial fibrosis including glandular alterations within fibrotic foci. Single glands and/or glandular nests can be affected (Kenney R M. Cyclic and pathologic changes of the mare endometrium as detected by biopsy, with a note on early embryonic death. J Am Vet Med Assoc 1978; 172:241-262).

The expression pattern of selected endometrial proteins, such as steroid hormone receptors, protein of proliferation intensity (Ki-67-antigen), the filaments vimentin, desmin, α-smooth muscle actin (α-actin), laminin and others have been studied (Walter I, Handler J, Reifinger M, Aurich C. Association of endometrosis in horses with differentiation of periglandular myofibroblasts and changes of extracellular matrix proteins. Reproduction 2001; 121:581-586, Hoffmann C, Ellenberger C, Mattos R C, Aupperle H, Dhein S, Stief B, Schoon H A. The equine endometrosis: new insights into the pathogenesis. Anim Reprod Sci 2009; 111:261-278).

These studies demonstrated that the affected endometrium seems unable to provide an appropriate environment for the correct expression of these proteins, when compared with healthy endometrium. However, until now, the etiology of endometrosis is not defined and no effective treatment is available.

Mesenchymal stem cells (MSCs) can be isolated from different adult tissues among which bone marrow and adipose tissue are more commonly used. These cells have the capacity to differentiate into several tissues of mesoderm and ectoderm origin, including bone, cartilage, tendon, muscle, adipose and neurons.

MSCs secret a diverse set of bioactive molecules, which are immunomodulatory (Aggarwal S, Pittenger M F. Human mesenchymal stem cells modulate allogeneic immune cell responses. Blood 2005; 105:1815-1822. Uccelli A, Prockop D J. Why should mesenchymal stem cells (MSCs) cure autoimmune diseases? Curr. Opin. Immunol. 2010; 22:768-774).

Other molecules released by MSCs provide regeneration and remodeling of injured tissue, through their trophic activities (Diekman et al., Chondrogenesis of adult stem cells from adipose tissue and bone marrow: induction by growth factors and cartilage-derived matrix. Tissue Eng Part A. 2010 February; 16(2):523-33, Caplan A I, Correa D. The MSC: an injury drugstore. Cell Stem Cell 2011; 1:11-15), which involve inhibition of apoptosis, stimulation of MSC-mediated angiogenesis by secretion of VEGF, as well as anti-scar formation activity (Sorrell J M, Baber M A, Caplan A I. Influence of adult mesenchymal stem cells on in vitro vascular formation. Tissue Eng Part A 2009; 15:1751-1761). Finally, MSCs secreted mitogens, which stimulate tissue-intrinsic progenitors to divide and appropriately differentiate (Wagner J, Kean T, Young R, Dennis J E, Caplan A I. Optimizing mesenchymal stem cell-based therapeutics. Curr Opin Biotechnol 2009; 20:531-536, Rehman J, Traktuev D, Li J, Merfeld-Clauss S, Temm-Grove C J, Bovenkerk J E, Pell C L, Johnstone B H, Considine R V, March K L. Secretion of angiogenic and antiapoptotic factors by human adipose stromal cells. Circulation 2004; 109:1292-1298).

Endometrosis is an age-associated, degenerative alteration of uterine glands and surrounding stroma, directly related to fertility problems. Because of the therapeutic properties MSCs, they have potential for treatment of this disease. Success of stem cell therapies depends at least, in part, on cell delivery, which should ensure wide cell distribution and homing within the injured site (Sorrell J M, Baber M A, Caplan A I. Influence of adult mesenchymal stem cells on in vitro vascular formation. Tissue Eng Part A 2009; 15:1751-1761).

To substitute for damaged cells and aiming at upgrading tissue integrity and function, a cell suspension is injected into the damaged tissue or into the blood circulation.

Depending on the pathology, treatment strategies can differ considerably (Wagner J, Kean T, Young R, Dennis J E, Caplan A I. Optimizing mesenchymal stem cell-based therapeutics. Curr Opin Biotechnol 2009; 20:531-536). A need exist for a method and therapy to treat and reduce the systems of these uterine disorders.

SUMMARY

According to an embodiment of the present disclosure mammalian females having uterine related infertility or pregnancy problems are treated by uterine transplantation of adipose tissue derived mesenchymal stem cells (AT-MSCs).

According to an additional embodiment of the present disclosure females having poor endometrium or a thin uterine lining, uterine polyps and fibroids, intrauterine adhesions and uterine cavity scar tissue are treated by uterine transplantation of adipose tissue derived MSCs.

In a further embodiment of the current disclosure MSCs are transplanted to the uterus of mammalian females suffering from uterine related infertility as method of improving the uterine environment prior to conception or in-vitro fertilization.

According to other embodiments of the present disclosure transplantation of MSCs into the uterine of mammalian females is performed according to the following procedure: a physician or operator introduces a disposable insemination pipette connected to a syringe containing MSCs through the cervix into the uterine body and the pipette is guided to a uterine horn. The plunger of the syringe is then depressed and the cell suspension is introduced into the uterus.

BRIEF DESCRIPTION OF THE FIGURES

The patent or application file contains at least one drawing executed in color. Copies of this patent or patent application publication with color drawing(s) will be provided by the Office upon request and payment of the necessary fee.

The accompanying figures, which are incorporated in and form a part of the specification, illustrate the embodiments of the present disclosure and, together with the description, serve to explain the principles of the disclosure.

DETAILED DESCRIPTION

Figure 1:
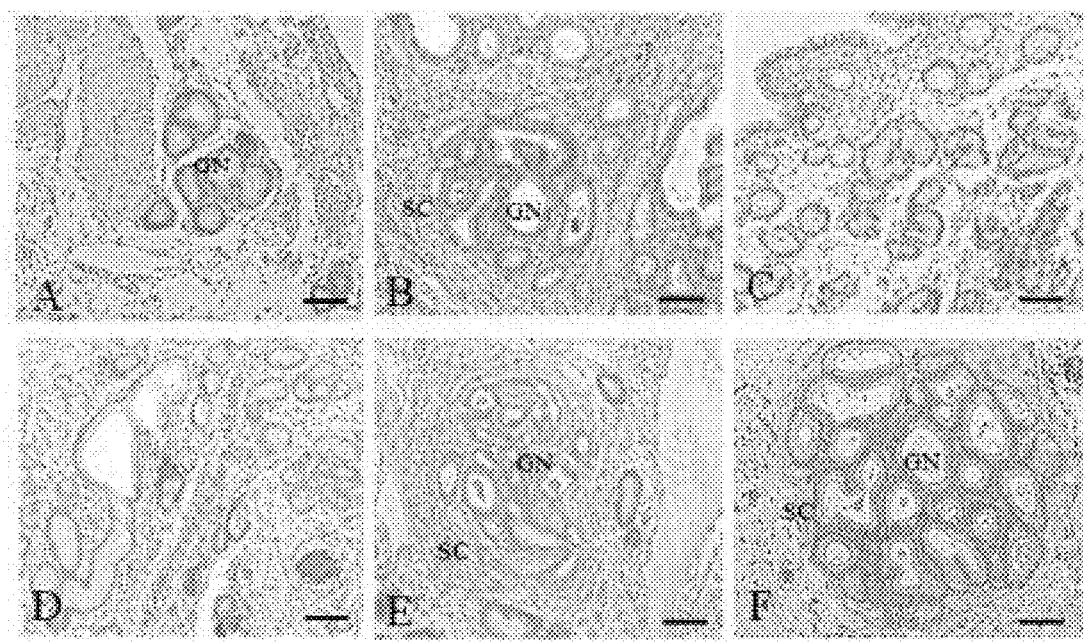
FIG. 1. Shows by histopathological analysis showing alterations of the mare's endometrium, which present different degree and quality of endometrosis. Inactive endometrosis is shown in: A) 01 (mares numbers, see material and methods section); B) 02; E) 05 and F) 06. Active destructive endometrosis is shown in: C) 03. Inactive destructive endometrosis is shown in: D) 04. GN—glandular nests, SC—stromal cells. Light microscopy (LM). Scale bars: A-E=200 µm; F=100 µm.

The inventors of the present disclosure disclose herein methods and therapies for treating mammalian females having endometriosis, poor endometrium, a thin uterine lining, uterine polyps and fibroids, intrauterine adhesions, uterine cavity scar tissue, uterine disorders or injury, uterine related infertility or uterine related pregnancy problems by administering via intrauterine transplantation adipose tissue derived mesenchymal stem cells (AT-MSCs) to a subject in need thereof.

In one embodiment of the present disclosure human female patients suffering from endometriosis, atypical endometrium or other uterine related disorders can be treated by intrauterine transplantation of AT-MSCs.

The present disclosure further provides a method of treatment of endometriosis in human females affected with said disorder, wherein said females are administered AT-MSCs.

Additionally the present method can be used in veterinary medicine in the treatment of mammalian females and in particular cows, sheep, goats and mares with endometriosis atypical endometrium or other uterine related disorders and infertility.

The method of the disclosure can be additionally used in mares suffering from equine endiometrosis wherein treatment is achieved by intrauterine transplantation of equine adipose tissue derived mesenchymal stem cells (eAT-MSCs).

According to an embodiment of the current disclosure, AT-MSCs, cryopreserved during two years in liquid nitrogen, are transplanted into the uterus of mammalian females with endometriosis, uterine disorders or injury, uterine related infertility or pregnancy problems directly after thawing without additional culturing in vitro.

In a further embodiment of the current disclosure AT-MSC are transplanted to the uterus of mammalian females suffering from uterine related infertility as method of improving the uterine environment prior to conception or in-vitro fertilization.

According to yet a further embodiment of the current disclosure the endometrial tissue of mammalian females with endometriosis, uterine disorders or injury, uterine related infertility or pregnancy problems is positively remodeled by intrauterine transplantation of AT-MSCs.

According to yet a further embodiment of the current disclosure the endometrial tissue of mammalian females with endometriosis is positively remodeled by intrauterine transplantation of AT-MSCs.

According to yet an additional embodiment of the current disclosure the endometrial tissue of mammalian females with endometriosis, uterine disorders or injury, uterine related infertility or pregnancy problems is positively remodeled up to 7 days following intrauterine transplantation of AT-MSCs.

According to yet an additional embodiment of the current disclosure the endometrial tissue of mammalian females with endometriosis is positively remodeled up to 7 days following intrauterine transplantation of AT-MSCs.

According to yet an additional embodiment of the current disclosure the endometrial tissue of mammalian females with endometriosis, uterine disorders or injury, uterine related infertility or pregnancy problems is positively remodeled up to 60 days following intrauterine transplantation of AT-MSCs.

According to yet an additional embodiment of the current disclosure the endometrial tissue of mammalian females with endometriosis is positively remodeled up to 60 days following intrauterine transplantation of AT-MSCs.

According to an embodiment of the present disclosure the uterine environment of mammalian females with endometriosis, uterine disorders or injury, uterine related infertility or pregnancy problems is stimulated by intrauterine transplantation of AT-MSCs.

According to an embodiment of the present disclosure uterine epithelial and periglandular stromal cells of mammalian females with endometriosis, uterine disorders or injury, uterine related infertility or pregnancy problems are stimulated by intrauterine transplantation of AT-MSCs.

According to an embodiment of the present disclosure the uterine expression of cytokeratin, vimentin, α-SMA and laminin of mammalian females with endometriosis, uterine disorders or injury, uterine related infertility or pregnancy problems is modulated by intrauterine transplantation of AT-MSCs.

According to an embodiment of the present disclosure the development of pathological processes in the uterine is prevented by intrauterine transplantation of AT-MSCs.

According to a further embodiment of the present disclosure the development of pathological processes in the uterine is prevented by modulation of expression of cytokeratin, vimentin, α-SMA and laminin by intrauterine transplantation of AT-MSCs.

According to an embodiment of the present disclosure the development of fibrotic regions in the endometrium is prevented or reduced by intrauterine transplantation of AT-MSCs.

According to an additional embodiment of the present disclosure uterine scarring is prevented or reduced by intrauterine transplantation of AT-MSCs.

According to an additional embodiment of the present disclosure uterine glandular epithelial cells proliferation is increased by intrauterine transplantation of AT-MSCs.

In a further embodiment the recurrence of uterine injury is prevented by intrauterine transplantation of AT-MSCs.

In yet a further embodiment the development of atypical morphological and functional differentiation of glandular and periglandular endometrial stromal cells is decreased or prevented by intrauterine transplantation of AT-MSCs.

In an embodiment of the present disclosure, treatment by intrauterine transplantation of AT-MSCs is combined with hormonal therapy.

In an embodiment of the present disclosure, treatment by intrauterine transplantation of AT-MSCs is combined with systemic stem cell therapies.

It has furthermore been shown that transplanted AT-MSCs can be allogeneic.

According to an embodiment of the present disclosure AT-MSCs are transplanted into uterine cavity of treated mammalian females using a method of minimally invasive MSCs delivery.

In an embodiment of the current disclosure, AT-MSCs cells are transplanted in to the uterus without application of immunosuppressive protocols.

In an embodiment of the current disclosure intrauterine AT-MSC transplantation application is performed during synchronized estrus.

In an additional embodiment of the current disclosure intrauterine AT-MSC transplantation application is performed during synchronized estrus with an insemination pipette through the cervix to the uterus body.

In yet a further embodiment of the current disclosure intrauterine AT-MSC transplantation application is performed during synchronized estrus by inserting an insemination pipette connected to a syringe containing a solution of AT-MSC cells through the cervix to the uterus body.

According to an embodiment of the present disclosure transplantation of MSCs into the uterine of mammalian females is performed according to the following procedure: a physician or operator introduces a disposable insemination pipette connected to a syringe containing MSCs through the cervix into the uterine body and the pipette is guided to a uterine horn. The plunger of the syringe is then depressed and the cell suspension is introduced into the uterus.

In a further embodiment of the current disclosure intrauterine AT-MSC transplantation application is performed during synchronized estrus by inserting an insemination pipette connected to a syringe containing $2 \times 10^7$ cells diluted in 20 ml of sodium chloride 0.9% through a sterile connector rubber through the cervix to the uterus body.

In a further embodiment of the current disclosure intrauterine AT-MSC transplantation application is performed during synchronized estrus by inserting an insemination pipette connected to a syringe containing $2 \times 10^7$ cells diluted in 20 ml of sodium chloride 0.9% through a sterile connector rubber through the cervix to the uterus body and subsequently the pipette is guided toward the tip of the right. The plunger of the syringe is depressed, introducing 10 ml of cells suspension. Then, the free end is placed on the left uterine horn and the remainder (10 ml of cells suspension) is infused. Immediately after, a second syringe containing 3 ml of sodium chloride 0.9% is coupled to the sterile pipette infused in order to ensure the total injection of volume contained in the pipette and in the connector. The pipette is then withdrawn from the vagina.

In an embodiment of the disclosure the pipette is guided to a uterine horn, assisted by ultra sound imaging or transrectal palpation. The pipette is guided to the right horn. In yet a further embodiment the pipette is guided to the left horn.

The preceding explanation of the disclosure has been offered for description purposes and is not designed to be comprehensive or to limit the disclosure to the exact disclosure, clearly numerous alterations and variants are possible in view of the above disclosure.

The present disclosure can be more clearly understood by reading the following examples that illustrate the present disclosure without any limitative character.

EXAMPLES

Example 1

Endometrosis Diagnosis

Endometrosis was confirmed in six mares, by histopathological (FIG. 1A-F) and protein (laminin, vimentin, smooth-muscle-α-actin, myogenin and estrogen receptor) expression analysis (FIG. 2A-D). FIGS. 1A, B and E, F demonstrate inactive endometrosis, which is represented by glandular nests (GN) with periglandular Stromal Cells (SC), characterized by spindle shaped morphology, hyperchromatous nuclei and an elongated cytoplasm. FIG. 1D represents a histopathology of a mare with inactive destructive endometrosis, characterized by single glands with inactive fibrotic SC which lie parallel arranged to the axis of the adjacent gland, multifocal destruction of single epithelial cells.

Additionally, expression pattern of proteins was studied: laminin, vimentin and a-smooth muscle actin (α-SMA) suggests the diagnosis of mixed types of endometrosis in studies mares (FIG. 2A-B). FIG. 2A reveals discontinuity of epithelial basal lamina, which is typical pattern of laminin expression in mares' endometrial glands with active destructive endometrosis. The expression of vimentin in damaged epithelia of glands (G) and in fibrotic stromal cells (FIG. 2B-C), and also the expression of microfilament α-SMA in endometrial glands are also observed (FIG. 2D). Myogenin and Estrogen Receptor (ER) expression were also verified in the uterus of mares committed by endometrosis. Both proteins showed specific staining limited to cell nuclei and predominant expression located in glandular nests (FIG. 2E-F).

Example 2 eAT-MSCs Labeling and Transplantation

The eAT-MSCs which were stored in liquid nitrogen for at least two years have been used in present study. Cells ($2 \times 10^7$) were thawed at 37° C. immediately before transplantation in the uterus of mares; they were promptly stained by fluorescent Vybrant CFDA-SE (DiI)—cell labeling solution. On FIG. 4 Vybrant stained eAT-MSCs are presented, which showed intracellular green fluorescence (FIG. 3A). eAT-MSCs transplantation into the uterus of mares was performed by protocol detailed in "Materials and Methods" section and as presented on FIG. 4.

Example 3 eAT-MSCs Distribution and Homing

In order to demonstrate homing of eAT-MSCs in the uterine tissue of mares, biopsies were obtained at day 7 and 21 (data not shown) after cell transplantation. After 60 days of cells transplantation, it was not possible to observe fluorescencently labelled cells. The absence of fluorescent labeling can be attributed to Vybrant's dye dilution following cells division. We observed the presence of labeled eAT-MSCs in three of four animals, which were submitted to cell transplantation procedure. In these three mares, eAT-MSCs were found nearly in all studied samples in both uterine horns and uterine body (FIG. 3B-L) except in the fourth horse (data not shown), which presented very severe stage of the disease according to pathological analysis (FIG. 1F). eAT-MSCs were found to home in periglandular space (FIGS. 3B-E and G-I) as well as in uterine glands (FIG. 3I-K); frequently they form clusters composed by 3-5 cells (FIGS. 3C, E and H). As expected, biopsies, obtained prior eAT-MSCs transplantation, and from animals which received only saline solution (control group) did not show any fluorescent labeling in endometrial tissue (FIG. 3F, L).

Example 4

Transplantation and Homing of eAT-MSCs

Figure 5:
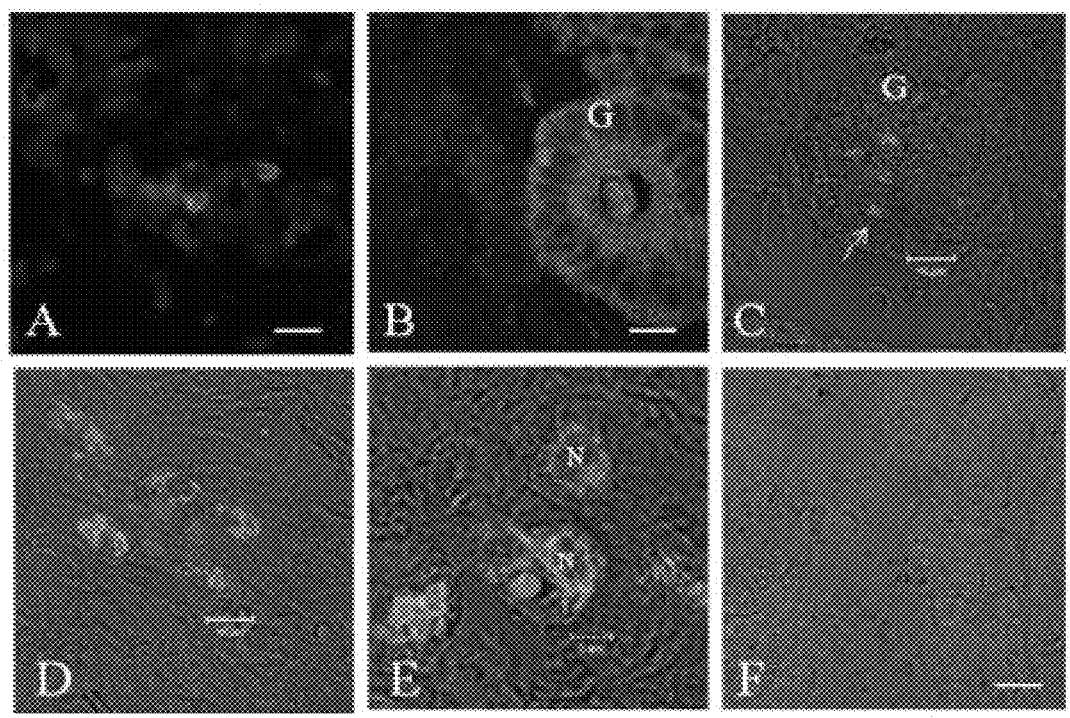
FIG. 5. Shows the presence of fluorescently labeled eAT-MSCs (green) in the uterus of mares after intrauterine infusion. A) Grafting of eAT-MSCs in the periglandular space B) eAT-MSC contribution into the whole uterine gland (G). The white arrow indicates uterine gland without eAT-MSCs. C) Incorporation of several eAT-MSC (white arrow) into uterine gland epithelia. D-E) eAT-MSCs localization in periglandular space. N-Nucleus. F) Control animals injected with only saline solution. A, B, F=nucleus stained by DAPI (blue). Confocal microscopy: Fluorescence (Fcm)+Digital Interference Contrast (DIC). A-B=Fcm. C-F=Fcm+DIC. Scale bars: A,C,D=10 µm; B, E, F=5 µm.

For eAT-MSCs transplantation in utero, cells (~2×10$^7$) were placed in a catheter and infused immediately. In order to confirm allogeneic eAT-MSCs homing in endometrial tissue, direct fluorescence was used. The presence of fluorescently labeled eAT-MSCs (green) in the uterus of mares was observed seven days after intrauterine cells infusion (FIG. 5 A-E), in FIG. 5F a control mare was infused only with saline solution. eAT-MSCs were visualized in periglandular space (FIG. 5 A, D, E), as well as in single glands (FIG. 5 B,C) in three mares. One of the mares, which presented advanced degree of chronic degenerative endometrosis, did not show any eAT-MSCs engraftment (data not shown).

Example 5

Figure 6:
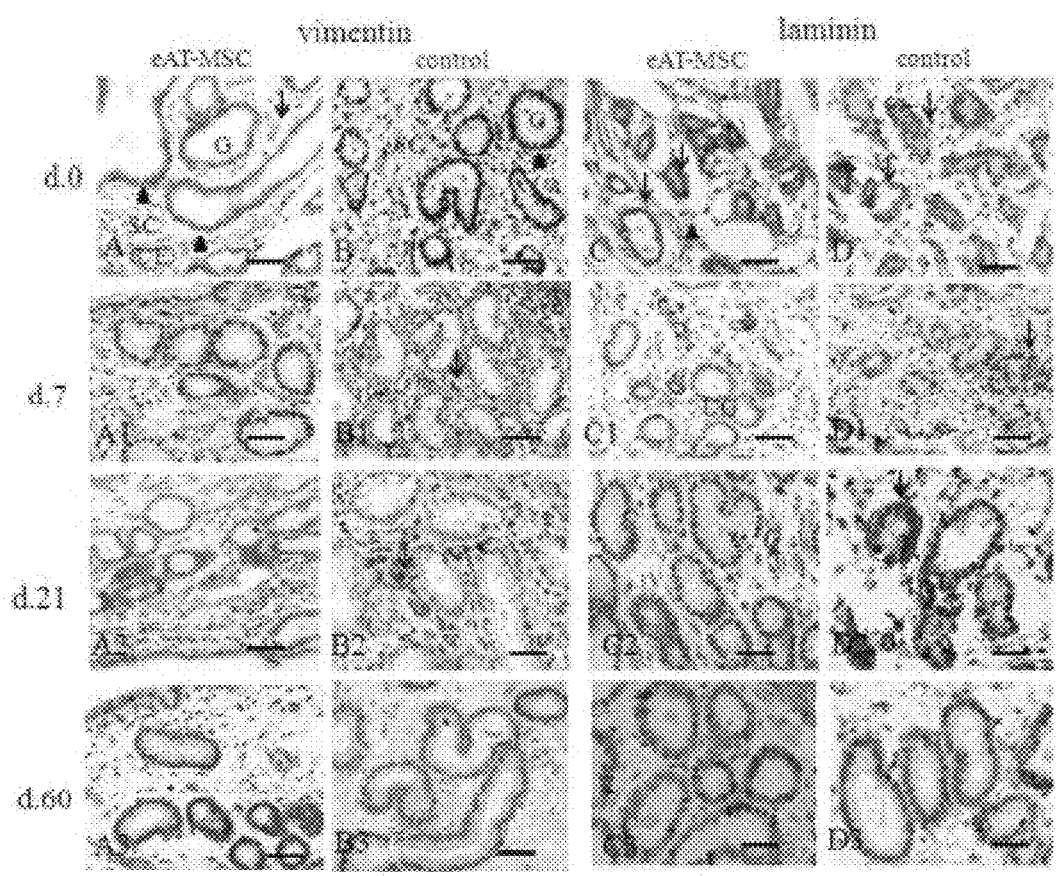
FIG. 6. Shows Vimentin and laminin expression before (at day 0) and after (at days 7, 21 and 60) eAT-MSCs intrauterine transplantation: A-A3 and D-D3—experimental; B-B3 and D-D3—control. A, B) At day 0, vimentin (black arrowheads) localized in damaged epithelia of glands (G) and in fibrotic stromal cells (SC, black arrows). Unaffected epithelia (UE) showed no signs of vimentin expression. A1-A3) At days 7, 21 and 60, the absence of vimentin expression. B1, B2) Vimentin expression is still observed (black arrows) at days 7 and 21, in control. B3) At day 60, control mares showed no signs of vimentin expression. C,D) At day 0, laminin demonstrated high discontinuity of epithelial basal lamina (black arrows) and a diffuse intracytoplasmatic laminin expression in metabolic active fibrotic stromal cells (black arrowheads); C1, C2) At days 7 and 21, unaffected glands (UG) with a diffuse intracytoplasmatic laminin expression were observed. C3) At day 60, the absence of vimentin expression was shown. D1, D2) At days 7 and 21, control maintains same pattern of laminin expression as in (D). D3) At day 60, laminin expression was not visualized in control. Light Microscopy (LM). Scale bars: A-C2=50 µm; C3, D2, D3=25 µm.
Figure 7:
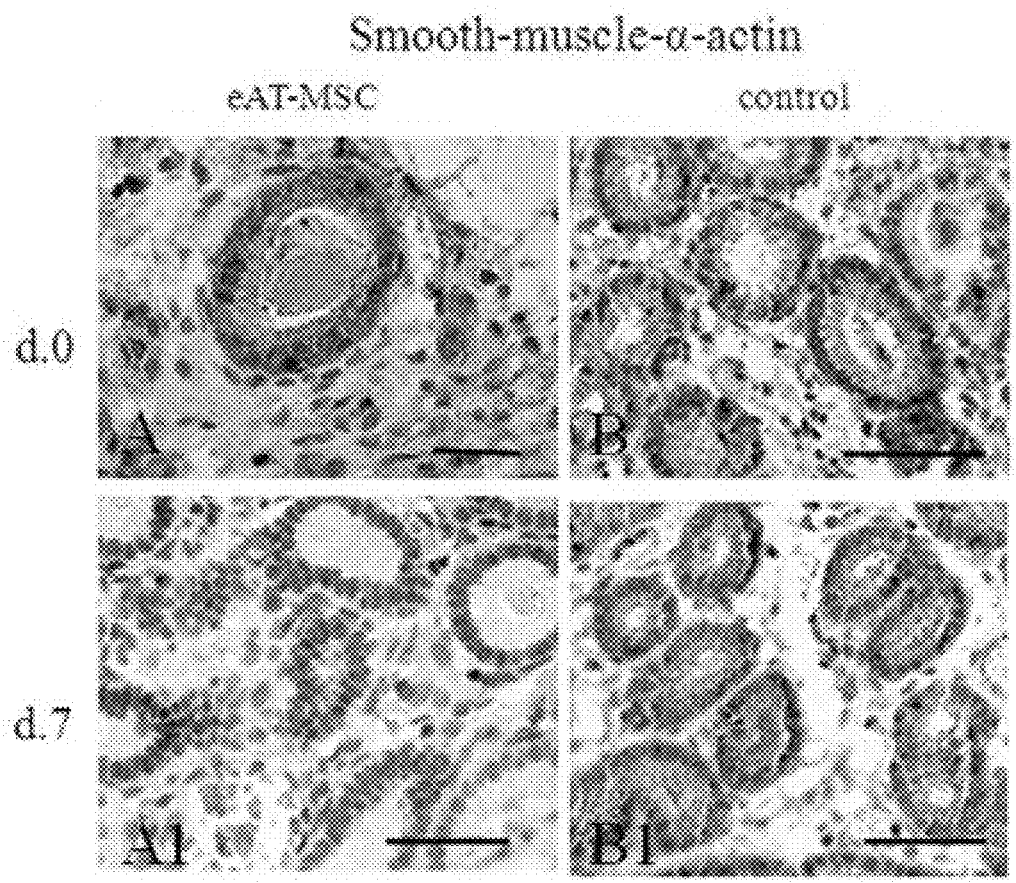
FIG. 7. Shows smooth-muscle-α-actin (SMA) expression before (at day 0) and after (at day 7) eAT-MSCs intrauterine transplantation. A, B) At day 0, SMA expression was observed in uterine glands (white arrowhead) and in periglandular fibroblasts (black arrow). A1) At day 7, SMA showed no signs of expression. B) Pattern of SMA expression is similar to A and B. LM. Scale bars: A=25 µm; A1, B, B1=50 µm.
Figure 8:
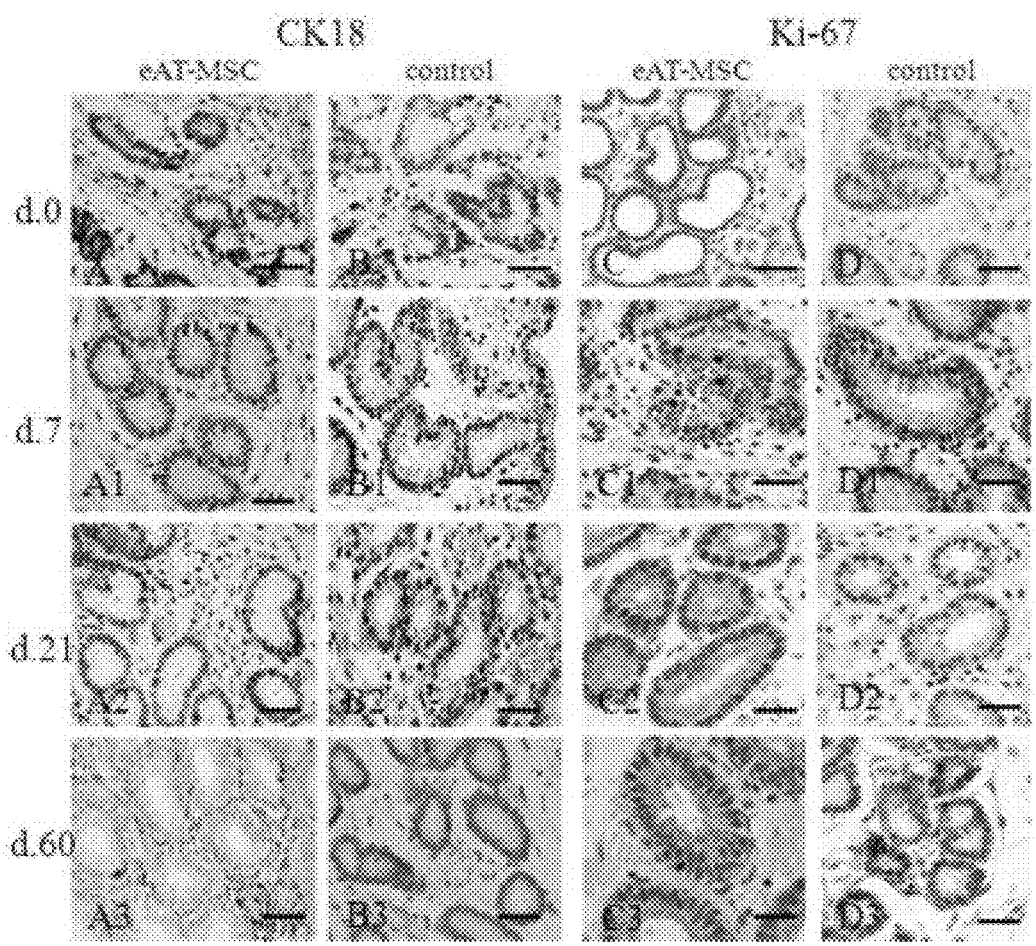
FIG. 8. Shows Cytokeratin 18 (CK18) and Ki-67 expression before (at day 0) and after (at days 7, 21 and 60) eAT-MSCs intrauterine transplantation: A-A3 and D-D3—experimental group; B-B3 and D-D3—control. A,B) At day 0, CK18 (black arrows) localized in damaged epithelia of glands (G). A1-A3) At days 7, 21 and 60, the absence of CK18 expression was observed. B1, B2) At days 7 and 21, CK18 expression was still observed (black arrows) in control. B3) At day 60, control mares showed no signs of CK18 expression. C, D) At day 0, none or a few Ki-67 positive cells were observed. C1, D1) At day 7, amount of Ki-67 positive cells (black arrow) was increased. C2, D2) At day 21, both groups showed positive Ki-67 staining. C3) At day 60, the expression of Ki-67 was still observed. D3) In control, the absence of Ki-67 expression. LM. Scale bars: A-D1=50 μm; C2, C3, D2, D3=25 μm.

Immunohistochemical Expression Study of Secretory Proteins Before and after eAT-MSC Transplantation In order to evaluate the benefits of eAT-MSCs transplantation and the engraftment of these cells in mares uterus with endometrosis, expression pattern of secretory proteins such as, vimentin, laminin, Ki-67, smooth-muscle-α-actin and cytokeratin 18 (CK18) has been analyzed (FIGS. 6-8).

Vimentin and Laminin

Figure 2:
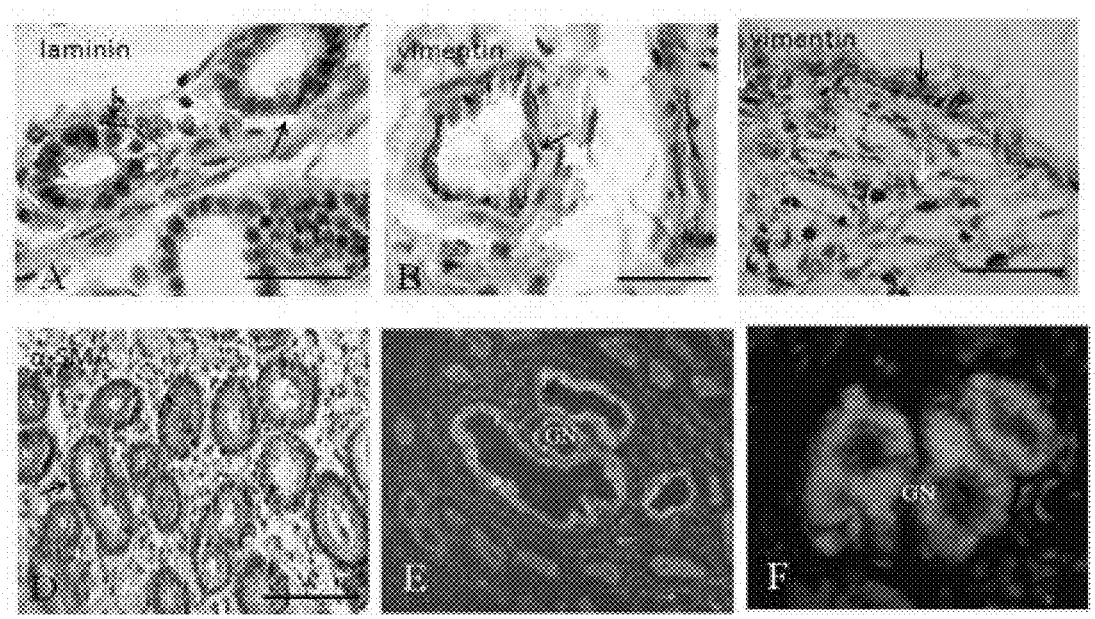
FIG. 2. Shows confirmation of endometriosis by protein expression pattern analysis of laminin, vimentin and α-smooth muscle actin (α-SMA) in mares' endometrium. Expression pattern is shown in: A) Laminin expression, with arrows showing discontinuity of epithelial basal lamina. B-C) Vimentin expression, with black arrows showing atypical vimentin expression in uterine glands and white arrows indicating vimentin positive fibrotic stromal cells. D) Atypical expression of α-SMA in uterine glands (black arrow). E-F) Expression of myogenin and ER in glandular nests (GN) is shown, respectively. E=Confocal microscopy: Fluorescence (Fcm)+Digital Interference Contrast (DIC); and F=Fcm A-D=LM. Scale bars: A-C=50 µm; D=100 µm.
Figure 3:
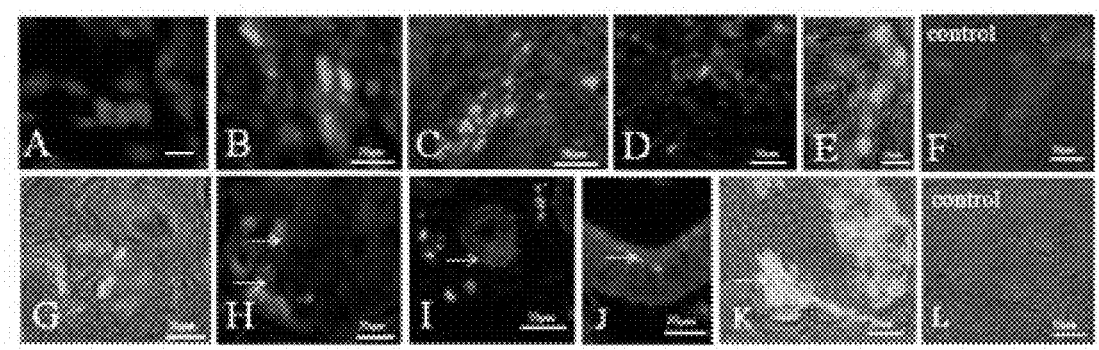
FIG. 3. Shows grafting of equine eAT-MSCs in endometrium of mares with endometriosis. A) Vybrant stained eAT-MSCs showed intracellular green fluorescence in vitro before transplantation into uterus. B-E) and G-I) Homing of eAT-MSCs in perigalandular space (green fluorescence): B) Uterine body; C-E) Uterine horns. G) eAT-MSCs localization in area of fibrous tissue in one of uterine horns. H) Homing of eAT-MSCs adjacent to basal membrane of uterine gland (white arrow). I-K) eAT-MSs incorporation in uterine glandular epithelia (white arrows). F and L) Control animals injected with saline solution: F) Periglandular space and L) Uterine gland. A-D, H-J=Fem. E,F,G,K,L=Fcm+DIC. Scale bars: A,E,F,L=10 µm; B,G,H,J,K=20 µm; C,D, I=50 µm.
Figure 4:
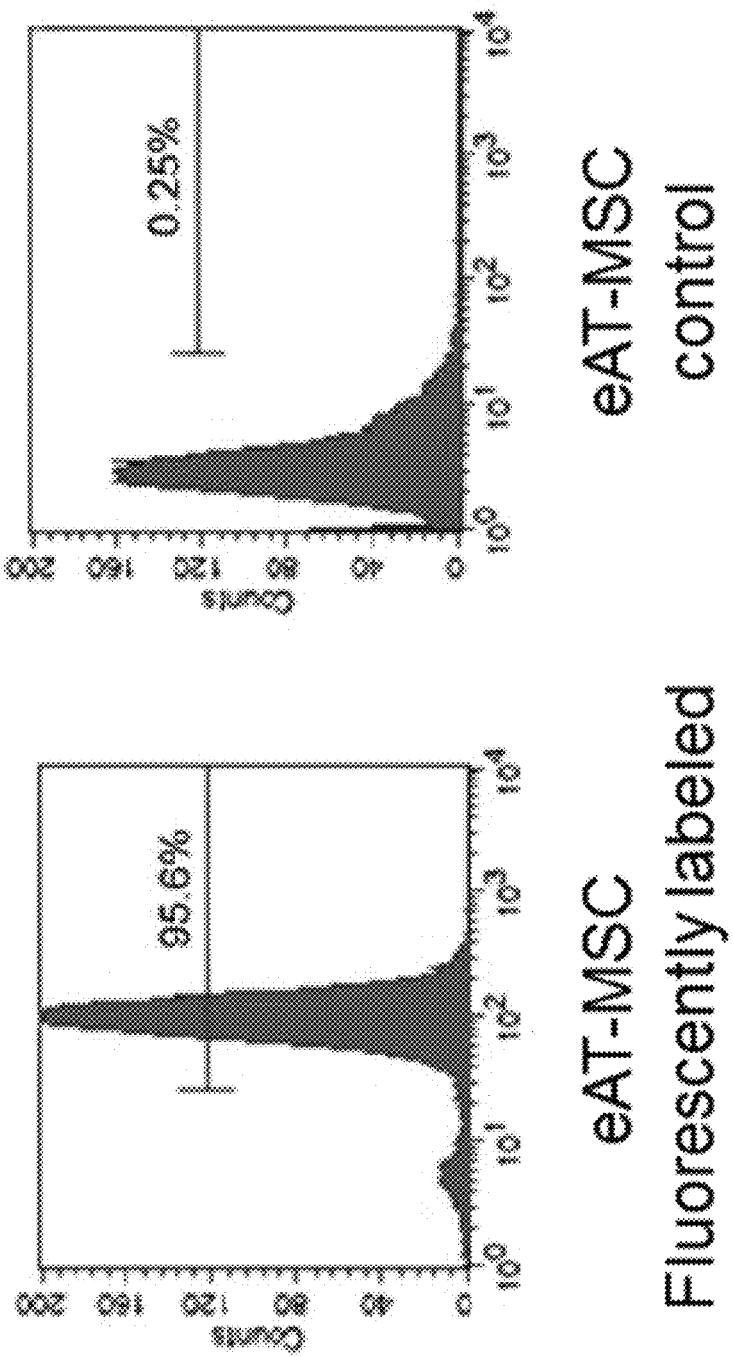
FIG. 4. Shows a flow cytometry analysis demonstrating efficiency of fluorescent labeling of eAT-MSCs: Vybrant stained eAT-MSCs; Non-stained cells; and Moment of eAT-MSCs application in mare.

Basal expression of vimentin in fibrotic gland epithelia and in fibrotic stromal cells was observed in experimental (FIG. 6A) and in control (FIG. 6B) groups before cells transplantation. Such basal expression of vimentin was no longer observed in the glandular epithelia and stromal cells at day 7 after cells transplantation (FIG. 2A1) and no changes was detected at days 21 and 60 (FIG. 6A2,A3). In control group, the expression of vimentin was strong in fibrotic stromal cells until day 21 (FIG. 6B1, B2) with no expression at day 60 (FIG. 6B3).

Laminin expression was intense and before cell transplantation it was noted a high discontinuity of epithelial basal lamina, as well as diffuse intracytoplasmatic expression in fibrotic stromal cells in all mares (FIG. 6C,D). In the biopsies obtained from mares which received the cells, diffuse intracytoplasmatic expression of laminin in fibrotic stromal cells, but not in epithelial basal lamina (FIG. 6C1, C2) was observed at days 7 and 21 after cell transplantation, with no expression at day 60 (FIG. 6C3). In control group, atypical expression pattern of laminin (FIG. 6D) was maintained until days 7 and 21 (FIG. 6D1, D2) and was no longer detected at day 60 (FIG. 6D3).

Smooth-muscle-α-actin

In all mares with endometrosis, the cystic dilated glands were coated by a distinct layer of cells positive to anti-α-SMA (FIG. 7A, B). Additionally, this protein expression was detected in fibroblasts surrounding fibrotic uterine glands (FIG. 7A). At day 7, in the biopsies of mares which received eAT-MSCs, the expression of anti-α-SMA in glands, no longer was evidenced (FIG. 7A1), while in control animals the expression of α-SMA was still present (FIG. 7B1). At days 21 and 60, the expression of this protein was no longer detected in both groups (data not shown).

Cytokeratin 18

CK18 expression was also evaluated. Similar to vimentin (FIG. 6A,B), CK18 was expressed in uterine glands of all animals before cell transplantation (FIG. 8A, B). Starting from day 7, this protein expression was no longer observed in experimental group (FIG. 8A1-A3), while in control group it was still expressed in uterine glands at day 7 and 21 (FIG. 8B1-B2), but not at day 60 (FIG. 8B3).

Ki-67-Antigen

In FIG. 8(C-D3) the expression of Ki-67 antigen in uterine glands and in periglandular stromal cells is presented in both, experimental (FIG. 8C-C3) and control groups (FIG. 8D-D3). At day 0, none or a few Ki-67 positive cells were observed in both groups (FIG. 8C, D). At day 7, both groups showed an increased quantity, but still a small amount of Ki-67 positive cells (FIG. 8C1 and D1). At day 21, Ki-67 positive cells significantly increased in both experimental (FIG. 8C2), and control (FIG. 8D2) groups. At day 60, the two groups (experimental and control) have registered progressive decrease of proliferative cells in glands (FIG. 8C3, D3). These qualitative data was confirmed by quantitative analysis of Ki-67 positive cells in glands (Table 2).

TABLE 2

| | Proliferation rate analyzed by Ki-67 antigen expression. | | | |
|---|---|---|---|---|
| Groups | 0 Days | 7 Days | 21 Days | 60 Days |
| Experimental Group n = 3 | 4.09% +/− 1.08% | 10.46% +/− 3.95% | 67.04% +/− 4.8% | 25.95% +/− 5.09% |
| Control Group n = 2 | 9.46% +/− 5.01% | 17.08% +/− 4.45% | 21.03% +/− 6.71% | 3.29% +/− 2.09% |

Example 6

Histological Characterization of Early Positive Remodeling of Endometrium

Figure 9:
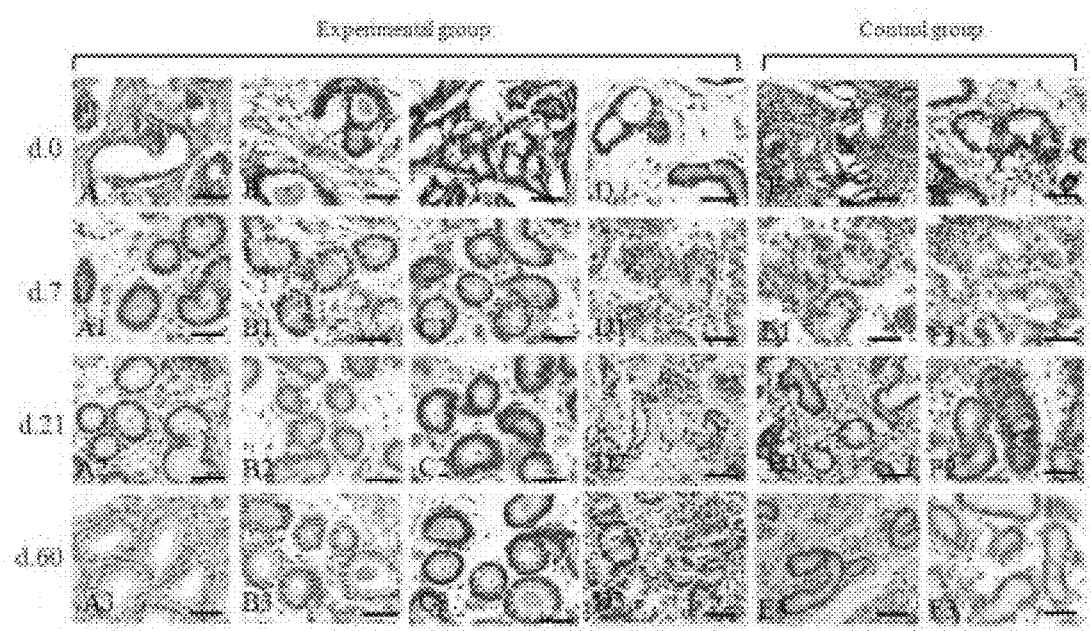
FIG. 9. Shows histological analysis of alterations in mares' endometrium following eATMSCs intrauterine transplantation. A-D3) Mares which received the cells. DE-F 3) Control mares. A-F) Morphology of endometrial surface prior eAT-MSCs intrauterine cells transplantation. A1-D1) Day 7 after eAT-MSCs intrauterine transplantation. A2-D2) Same as in (A1-D1) at day 21. A3-D3) Same as in (A1-D1) at day 60. E1-F3) Respective controls. LM. Scale bars: A-F3=50 μm.

Morphological characteristics of representative specimens of the biopsies obtained from mares with endometrosis are presented on FIG. 9 A-F. The foci of endometriosis, including periglandular stromal cells ("fibrotic stromal cells") and affected glandular epithelia, as well as neighbored unaltered glands, were taken in consideration. In all animals, single glands and/or glandular nests were affected. Following eAT-MSCs transplantation, positive histological changes were observed in three mares (FIG. 9 A1-C3). One mare, which presented more severe degree of endometrosis and received the cells, did not show cell incorporation into endometrium (data not shown) as well as morphological improvement (FIG. 9D-D3).

Control animals showed relatively unaltered pattern of endometrial histology (FIG. 9E1-F3).

DISCUSSION

In order to evaluate the effects of MSCs on disturbed endometrium microenvironment in mares during breeding season, allogeneic eAT-MSCs were transplanted into uterus of mares with endometrosis. Before eAT-MSCs transplantation, histological studies of the endometrium of all animals enrolled in the present investigation have been carried out and atypical morphological differentiation of glandular and periglandular endometrial stromal cells was demonstrated. According to (Hoffmann C, Ellenberger C, Mattos R C, Aupperle H, Dhein S, Stief B, Schoon H A. The equine endometrosis: new insights into the pathogenesis. Anim Reprod Sci 2009; 111:261-278), such altered protein expression pattern of vimentin, laminin, smooth-muscle-α-actin and CK18 was observed in endometrium of mares, thus confirming endometrosis.

Incorporation of these cells following intrauterine transplantation in mares' uterus was shown using the method of direct immunofluorescence. The cells home into periglandular space and in few cases contributed significantly into glandular epithelia improvement. As shown previously, the co-expression of cytokeratin and vimentin is normal during the proliferation phase in human but not in equine endometrium (Norwitz E R, Fernandez-Shaw S, Barlow D H, Starkey P M. Expression of intermediate filament in endometrial glands changes with the onset of pregnancy and in endometriosis. Hum Reprod 1991; 6:1470-1473, Tabibzadeh S. Human endometrium: an active site of cytokine production and action. Endocr Rev 1991; 12:272-290, Nisolle M, Casanas-Roux F, Donnez J. Coexpression of cytokeratin and vimentin in eutopic endometrium and endometriosis throughout the menstrual cycle: evaluation by a computerized method. Fertil Steril 1995; 64:69-75).

The co-expression of both of these proteins in epithelial cells has been observed in different tumors and for many years, CK18 has been recognized as an epithelial marker in histopathology diagnostic (McNutt M A, Bolen J W, Gown A M, Hammar S P, Vogel A M. Coexpression of intermediate filaments in human epithelial neoplasms. Ultrastruct Pathol 1985; 9:31-43-29, Dabbs D J, Geisinger K R, Norris H T. Intermediate filaments in endometrial and endocervical carcinomas. The diagnostic utility of vimentin patterns. Am J Surg Pathol 1986; 10:568-576). Accordingly, we observed the co-expression of these proteins in endometrium of all mares with endometrosis. Following eAT-MSCs transplantation, the co-expression of these markers was no longer observed in mares' endometrium, when compared with control group, suggesting positive effect of eATMSCs transplantation on expression pattern of these proteins.

The analysis of expression pattern of such proteins as α-SMA, laminin and Ki-67 antigen support aforementioned data. It has been shown that stromal cells of destructive endometrosis, in particular in the active destructive endometrosis, tended to express more α-SMA. It is of common knowledge that local stimuli induces smooth muscle differentiation in resident fibroblasts and neighboring epithelial or mesenchymal cells can produced these stimuli. Accordingly, differentiation of periglandular cells to myofibroblasts, leading to a comparable histopathology, was also reported for fibrotic dilated glands of the human endometrium (Czernobilsky B, Remadi S, Gabbiani G. Alpha-smooth muscle actin and other stromal markers in endometrial mucosa. Virchows Archiv 1993; 422:313-317).

In our study, the expression of microfilament α-SMA in uterine glands was observed before eAT-MSCs transplantation in all studied animals. However, at day 7, the expression of α-SMA was no longer observed in uterine glands of animals which received eAT-MSCs.

Laminin are known to be the major protein in the basal lamina, which is a protein network foundation for most cells and organs. The laminin influence cell differentiation, migration, adhesion as well as phenotype and survival (Timpl R, Rohde H. Laminin—a glycoprotein from basement membranes. J Biol Chem 1979; 254: 9933-9937).

After eATMSCs transplantation, atypical laminin localization in experimental group was positively modified at day 7, while in control endometrium such alteration did not occur. Atypical laminin localization in both groups before eAT-MSCs transplantation can be explained by the fact that myofibroblasts are known to build up an incomplete layer of basal lamina on their cell surface, which is known to maintain smooth muscle cells in a differentiated stage (Schmitt-Gräf A, Desmoulière A, Gabbiani G. Heterogeneity of myofibroblast phenotypic features: an example of fibroblastic cell plasticity. Virchows Archiv 1994; 425:3-24).

Ki-67 antigen is an excellent marker to determine the growth cell fraction of a given cell population. An altered intensity of cell proliferation (which also depends on the steroid cycle) within the fibrotic foci during the estrous cycle was shown to be obvious (Hoffmann C, Ellenberger C, Mattos R C, Aupperle H, Dhein S, Stief B, Schoon H A. The equine endometrosis: new insights into the pathogenesis. Anim Reprod Sci 2009; 111:261-278).

The effect of extrinsic human MSCs on the viability, proliferation and differentiation of intrinsic cells in the local of injury was demonstrated over past years (Caplan A I. What's in a name? Tissue Eng Part A 2010; 16:2415-2417, Caplan A I, Correa D. The MSC: an injury drugstore. Cell Stem Cell 2011; 1:11-15). Accordingly, our data demonstrate that the amount of Ki-67 positive cells was significantly higher in endometrium of mares treated with eAT-MSCs in comparison with untreated animals (Table 2).

After eAT-MSCs transplantation at day 7, early morphological remodeling of the endometrium was observed, when compared with untreated mares. Morphological alterations in endometrium were escorted by changes in analyzed proteins expression pattern in treated animals, but not in control mares, which continued to present atypical protein expression pattern until day 21. Taken together, our data provide evidences of morphological and functional benefits of MSCs transplantation into mares with endometrosis.

The number of empty seasons is one of the factors that can influence the incidence of endometrosis. The fact that one animal with advanced degree of endometrial degeneration has not responded to the treatment, suggests the preventive use of stem cells therapy which can slow down the degeneration process that occurs with mares which failed to be pregnant in the previous breeding season.

CONCLUSION

Herein, we showed for the first time that allogeneic eAT-MSCs, which were cryopreserved during two years in liquid nitrogen, can be used directly after thawing without additional culturing in vitro. These equine cells can be transplanted without application of immunosuppressive protocols, while presenting successful and efficient homing in mares' endometrium. Additionally, following intrauterine transplantation, eAT-MSCs were able to induce early (at day 7) and prolonged (until day 60) positive remodeling of endometrial tissue of these mares with endometrosis. These extrinsic allogeneic eAT-MSCs were able to stimulate local environment, composed by epithelial and periglandular stromal cells, and to modulate the expression of cytokeratin, vimentin, α-SMA and laminin, thus avoiding further development of pathological processes, which leads to the formation of highly fibrotic regions of the horse endometrium.

Our data suggest that these cells, similar to human MSCs from bone marrow, act through multiple mechanisms, such as homing in fibrotic periglandular and glandular space, modulation of the expression pattern of studied proteins and increase of glandular epithelial cells proliferation, thus providing anti-scaring effect.

It is important to note, that local therapy is designed to prevent a local recurrence of the injury. Our study targets a local effect of MSCs on injury, which takes place in endometrium of mares. However, atypical morphological and functional differentiation of glandular and periglandular endometrial stromal cells seems to appear as a result of systemic effect (an adverse health effect), that takes place at a location distant from mares' endometrium. Therefore, logic rationality suggests that the combination between local and systemic stem cell therapies may provide more efficient tool to combat endometrosis, one of the major cause for equine infertility.

MATERIALS AND METHODS FOR EXAMPLES

Animals

Six cycling healthy mares of various breeds, between 6 and 21 years old, with different degree of endometrosis were used. These mares were part of an experimental herd and were maintained at the Faculty of Veterinary Medicine, Federal University of Rio Grande do Sul, in an open field, supplemented with oats and alfalfa hay, with ad libitum access to water.

An endometrial biopsy was taken before the beginning of the experiment and used to classify the mares, of which three were classified as grade IIb (mares 03, 04 and 05), and three as grade III (mares 01, 02 and 06), according to [Kenney R M, Doig P A. Equine endometrial biopsy. Current Therapy in Theriogenology 1986: 723-729].

A mare from each grade (mares 02 and 03) was used as control during cell transplantation experiments. Mares were examined for reproductive soundness, including evaluation of perineal conformation, palpation per rectum and ultrasound of the genital tract, vaginal examination with speculum, bacteriological cultures and cytology of the endometrium. Only clinically normal mares with negative cytology and negative cultures were used.

Time of estrus was synchronized in mares with prostaglandin F2α (Lutalyse 5 mg im—Pharmacia Brasil Ltda., São Paulo, SP, Brasil). The presence of a dominant follicle (≥35 mm) at the time of cells transplantation was confirmed.

Cells

Equine adipose tissue-derived mesenchymal stem cells (eAT-MSC), previously isolated and characterized by our group [Mambelli L I, Santos E J, Frazão P J, Chaparro M B, Kerkis A, Zoppa A L, Kerkis I. Characterization of equine adipose tissue-derived progenitor cells before and aftercryopreservation. Tissue Eng Part C Methods 2009; 15:87-94], were used in order to improve endometrial tissue affected by endometrosis. These cells were cryopreserved in liquid Nitrogen during two years. The cells were thawed and used immediately for fluorescent labeling and transplantation.

Fluorescent eAT-MSCs Labeling

For cell labeling, Vybrant® CFDA SE Cell Tracer Kit fluorescent-nanocristal dye (green) (Invitrogen, Carlsbad, Calif., USA; V12883) was used. CFDA SE 10 mM stock solution was prepared immediately prior to use by solving the contents of one vial (Component A) in 90 μL of the high-quality DMSO provided in the kit (Component B). Next, stock solution was diluted in phosphate-buffered saline (PBS) until reach the desired working concentration of 25 μM. eAT-MSCs were thawing just before staining following washing twice in DMEM-HG. Cell pellets were obtained by centrifugation (1000 rpm, 5 min) and the supernatant was aspirated. Next, eAT-MSCs were gently resuspended in pre-warmed (37° C.) PBS containing the probe and incubated for 15 minutes at 37° C. Cells were re-pelleted by centrifugation and resuspended in 20 ml of fresh pre-warmed physiologic solution 0.9% for further infusion into mares' uterus.

Experimental Cell Transplantation

The procedure of eAT-MSCs application was performed during synchronized estrus according to following procedure. After cleaning the perineal area, the operator wearing a sterile insemination glove introduced a disposable insemination pipette through the cervix to the uterus body. In order to avoid eventual contaminants the gloved hand was placed over the tip of the pipette during its introduction into the vagina. At this time, the pipette was guided toward the tip of the right horn helped by rectal palpation. The pipette was connected to the syringe containing $2 \times 10^7$ cells diluted in 20 ml of sodium chloride 0.9% through a sterile connector rubber. The plunger of the syringe was slowly depressed, introducing 10 ml of cells suspension. Then, the free end was placed on the left uterine horn and the remainder (10 ml of cells suspension) was infused. Immediately after, a second syringe containing 3 ml of sodium chloride 0.9% was coupled to sterile pipette infused in order to ensure the total injection of volume contained in the pipette and in the connector. The pipette was slowly withdrawn from the vagina.

The two controls mares were infused with 20 ml of sodium chloride 0.9% with, 10 ml in each horn tip, performing the same technique used to cell transplantation. A biopsy from the uterine body and left and right horns from treated and control mares was collected after 7, 21 and 60 days of the inoculation. A total of 60 endometrial uterine biopsies from the six mares have been analyzed in a blind manner.

Histology

Uterine biopsies were fixed in 10% buffered formalin, embedded in paraplast, sectioned at 4-5 μm and stained with Hematoxylin and Eosin (HE). The degree of endometrosis was analyzed according to [Kenney R M. Cyclic and pathologic changes of the mare endometrium as detected bybiopsy, with a note on early embryonic death. J Am Vet Med Assoc 1978; 172:241-262.].

All specimens showed signs of endometrosis varying in quantity, degree (mild to severe) and quality (active or inactive).

Immunohistochemistry

The peroxidase anti-peroxidase (PAP) method was used for immunohistochemistry. Tissue sections were mounted on superfrost slides (Life Science Int. GmbH, Frankfurt/Main, Germany). The paraffin wax sections were rehydrated and endogenous peroxidase activity was inhibited by 3% H2O2 in methanol (30 min).

Primary antibodies were diluted in TBS (Tris-buffered saline) with 1% BSA (bovine serum albumin). Depending on the antibody, different dilutions and pretreatments were applied and are summarized in Table 1. Primary monoclonal antibody cross-reacting with mouse antihuman CK18, as well as polyclonal antibodies rabbit antihuman Ki-67-antigen, rabbit antimouse laminin, rabbit antihuman fibronectin and goat antihuman vimentin were incubated at 4° C. overnight. Negative control sections were treated with TBS/BSA only. Rat antimouse (Dianova GmbH, Hamburg, Germany) and pig antirabbit IgG (Dako Diagnostika GmbH, Hamburg, Germany) were used as secondary antibodies and, as PAP-complex, served 1:500 diluted mouse PAP (Dianova GmbH, Hamburg, Germany) and rabbit PAP (Dako Diagnostika GmbH, Hamburg, Germany), respectively. Both were incubated at room temperature for 30 min. Slides were developed in DAB (diaminobenzidinetetrahydrochloride—Fluka Feinchemikalien Neu Ulm, Germany) and counterstained with HE.

TABLE 1

Antibodies used in immunohistochemistry.

| Primary antibodies | Host | Type | Dilution | Source |
|---|---|---|---|---|
| α-Actinin[1] | Mouse | Monoclonal | 1:200 | Chemicon, CA, USA |
| CD10[1] (clone 56C6) | Mouse | Monoclonal | 1:25 | AbCam, San Francisco, USA |
| Cytokeratin 18[1] | Mouse | Monoclonal | 1:200 | Cell Marque, CA, USA |
| ER[1] (clone 14C8) | Mouse | Monoclonal | 1:100 | Thermo Scientific, CA, USA |
| Ki-67[1] | Rabbit | Polyclonal | 1:100 | Santa Cruz Biotechnology CA, USA |
| Laminin[1] | Rabbit | Polyclonal | 1:25 | AbCam, San Francisco, USA |
| Vimentin[2] (clone C20) | Goat | Polyclonal | 1:50 | San Cruz Biotechnology, CA, USA |

[1]IgG polyclonal goat anti-mouse + goat anti-rabbit HRP (secondary antibody)
[2]Polyclonal rabbit anti-goat HRP (secondary antibody)

In order to interpret immunohistochemical results of the fibrotic foci, unaltered endometrial structures within the same specimens were used as controls. The proteins expression was detected using a Carl Zeiss Axioplan fluoromicroscope (LSM 410, Zeiss, Jena, Germany) Digital images were acquired with CCD camera (Applied Imaging model ER 339) and the documentation system used was Cytovision v. 2.8 (Applied Imaging Corp.—Santa Clara, Calif., USA).

Confocal Microscopy

Images were collected using an LSM 510 (Zeiss) laser scanning confocal microscope. FITC was excited by argon-ion laser set at 488 nm, and the emitted light filtered using a 505-nm (FITC) long pass filter. Sections were taken at approximately the mid-height level of the cells.

Statistical Analysis

Ki-67 positive cell density may not be uniform in the biopsy; therefore epithelial cell proliferation rate within the glands was assessed by the Ki-67 stained cells, in 250 cells, of five different fields. The mean called proliferation index (P) and pattern deviation (Mean±SD), as well as the median of positive nuclear stained cells in the 5 fields were calculated. The differences between treated and untreated animals are shown in percentage.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

I claim:

1. A method of treating a mammalian female subject having a disorder selected from the group consisting of: endometriosis, atypical endometrium, poor endometrium, thin uterine lining, uterine polyps and fibroids, intrauterine adhesions, uterine cavity scar tissue, uterine disorders or injury, uterine related infertility or pregnancy problems, the method comprising transplanting adipose tissue derived mesenchymal stem cells (AT-MSCs) into the uterus of the mammalian female in need thereof, wherein transplanting adipose tissue derived AT-MSCs is performed according to the following procedure: a physician or operator introduces an insemination pipette connected to a syringe containing AT-MSCs through the cervix into the uterine body and the pipette is guided to a uterine horn, the syringe comprising a plunger which is depressed and the AT-MSCs are introduced into the uterus.

2. The method of claim 1, wherein the mammalian female is human.

3. The method of claim 2, wherein the disorder is endometriosis.

4. The method of claim 1, wherein the subject is an animal.

5. The method of claim 4, wherein the animal is selected from the group consisting of a cow, a sheep, a goat, and a mare.

6. The method of claim 5, wherein the animal is a mare suffering from equine endometriosis.

7. The method of claim 1, wherein the transplanted AT-MSCs were cryopreserved in liquid nitrogen.

8. The method of claim 7, wherein the AT-MSCs are transplanted directly after thawing without additional culturing in vitro.

9. The method of claim 1, wherein the method improves the uterine environment prior to conception or in-vitro fertilization.

10. The method of claim 1, wherein the method positively remodels the endometrial tissue of the mammalian subject.

11. The method of claim 10, wherein remodeling the endometrial tissue is up to 7 days following intrauterine transplantation of AT-MSCs.

12. The method of claim 10, wherein the method positively remodels the endometrial tissue up to 60 days following intrauterine transplantation of AT-MSCs.

13. The method of claim 1, wherein the method stimulates the uterine environment of mammalian females having endometriosis, uterine disorders or injury, uterine related infertility or pregnancy problems.

14. The method of claim 1, further comprising stimulating uterine epithelial and periglandular stromal cells of mammalian females with endometriosis, uterine disorders or injury, uterine related infertility or pregnancy problems.

15. The method of claim 1, further comprising modulating the uterine expression of proteins selected from the group consisting of cytokeratin, vimentin, α-SMA and laminin in mammalian females with endometriosis, uterine disorders or injury, uterine related infertility or pregnancy problems.

16. The method of claim 1, wherein the method decreases or prevents the development of pathological processes in the uterine.

17. The method of claim 1, wherein the method decreases or prevents the development of fibrotic regions in the endometrium.

18. The method of claim 1, wherein the method decreases or prevents uterine scarring.

19. The method of claim 1, wherein the method increases uterine glandular epithelial cells proliferation.

20. The method of claim 1, wherein the method decreases or prevents the recurrence of uterine injury.

21. The method of claim 1, wherein the method reduces or prevents the development of atypical morphological and functional differentiation of glandular and periglandular endometrial stromal cells.

22. The method of claim 1 wherein transplanting adipose tissue derived AT-MSCs in the uterus is done prior to hormonal therapy, concurrently with hormonal therapy or subsequently to hormonal therapy.

23. The method of claim 1, further comprising administrating to the subject one or more systemic stem cell therapies.

24. The method of claim 1, wherein the AT-MSCs are allogeneic.

25. The method of claim 1, wherein transplanting adipose tissue derived AT-MSCs is performed without application of immunosuppressive protocols.

26. The method of claim 1, wherein transplanting adipose tissue derived AT-MSCs is performed during synchronized estrus by inserting an insemination pipette connected to a syringe containing at least $2\times10^7$ cells diluted in at least 18 ml of 0.7% to 11% sodium chloride through a sterile connector rubber through the cervix to the uterus body.

27. The method of claim 26, wherein the pipette is subsequently guided toward the tip of the uterine horn and the plunger of the syringe is depressed, introducing approximately half of the AT-MSCs, followed by introducing the approximately half of the AT-MSCs on the remaining uterine horn and a second syringe comprising 2 to 5 ml of sodium chloride of about 0.9% is coupled to the sterile pipette infused to ensure total injection of volume contained in the pipette and in the connector.

28. A method of treating a mammalian female subject having a disorder selected from the group consisting of: endometriosis, atypical endometrium, poor endometrium, thin uterine lining, uterine polyps and fibroids, intrauterine adhesions, uterine cavity scar tissue, uterine disorders or injury, uterine related infertility or pregnancy problems, the method comprising transplanting AT-MSCs into the uterus of the mammalian female in need thereof, wherein transplanting adipose tissue derived AT-MSCs is performed during synchronized estrus with an insemination pipette through the cervix to the uterus body.

29. A method of treating a mammalian female subject having a disorder selected from the group consisting of: endometriosis, atypical endometrium, poor endometrium, thin uterine lining, uterine polyps and fibroids, intrauterine adhesions, uterine cavity scar tissue, uterine disorders or injury, uterine related infertility or pregnancy problems, the method comprising transplanting AT-MSCs into the uterus of the mammalian female in need thereof, wherein intrauterine transplantation is performed during synchronized estrus with an insemination pipette connected to a syringe containing a solution of AT-MSC cells through the cervix to the uterus body.

* * * * *